United States Patent [19]

Matsumura et al.

[11] Patent Number: 5,723,708
[45] Date of Patent: Mar. 3, 1998

[54] METHOD FOR PRODUCING CYCLOPENTADIENES

[75] Inventors: Yasuo Matsumura; Kazuharu Suyama, both of Yokohama; Yoshihisa Inomata, Kawasaki, all of Japan

[73] Assignee: Nippon Petrochemicals Company, Limited, Tokyo, Japan

[21] Appl. No.: 534,817

[22] Filed: Sep. 27, 1995

[30] Foreign Application Priority Data

| Sep. 29, 1994 | [JP] | Japan | 6-261995 |
| Sep. 29, 1994 | [JP] | Japan | 6-261996 |
| Dec. 29, 1994 | [JP] | Japan | 6-340509 |

[51] Int. Cl.$^6$ .................. C07C 1/20; C07C 1/207; C07C 13/15; C07C 13/28
[52] U.S. Cl. .................. 585/358; 585/350; 585/357; 585/360; 585/365; 585/603; 585/604; 585/607; 423/416; 568/338; 568/382
[58] Field of Search .................. 585/350, 357, 585/358, 360, 365, 603, 604, 607; 432/416; 568/338, 382

[56] References Cited

U.S. PATENT DOCUMENTS

| 4,412,088 | 10/1983 | Gruber et al. | 585/23 |
| 4,568,782 | 2/1986 | Pagnotta et al. | |
| 4,677,238 | 6/1987 | Pedersen et al. | |
| 4,967,033 | 10/1990 | Mahaim | 585/358 |
| 5,329,056 | 7/1994 | Belmont | 585/358 |
| 5,414,173 | 5/1995 | Garces et al. | 585/357 |
| 5,434,324 | 7/1995 | Lee et al. | 585/357 |

FOREIGN PATENT DOCUMENTS

| 62-72630 | 4/1987 | Japan. |
| 6-135858 | 5/1994 | Japan. |

OTHER PUBLICATIONS

Die Makromolekulare Chemie, 127, pp. 78–93 (1969) no month available.

*Primary Examiner*—Elizabeth A. Wood
*Attorney, Agent, or Firm*—Fisher, Christen & Sabol

[57] ABSTRACT

A method for producing cyclopentadienes which comprises the step of cyclodehydration of an unsaturated carbonyl compound having a specific chemical structure in a vapor phase in the presence of a specific solid acid catalyst. The cyclopentadienes of the invention can be produced in a high yield from inexpensive starting materials through a simplified reaction process and are useful as intermediate compounds for organic synthesis.

7 Claims, No Drawings

METHOD FOR PRODUCING CYCLOPENTADIENES

BACKGROUND OF THE INVENTION (1) Field of the Invention

This invention relates to a novel method for industrially producing cyclopentadienes which are useful as intermediate compounds for organic synthesis.

(2) Description of the Prior Art

Taking 1,3-dimethylcyclopentadiene as an example of cyclopentadienes, the prior art will be described.

Various methods for producing 1,3-dimethylcyclopentadiene have hitherto been proposed. Among them, as examples of methods for producing the same from industrially available raw materials are exemplified as follows:

(1) a method which comprises the step of reacting dicyclopentadiene with methanol in the presence of an alkali metal oxide (Japanese Laid-Open Patent Publication No. 62-72630 (1987), (2) a method which comprises the step of reacting a Grignard reagent with 3-methyl-2-cyclopenten-1-one which is obtained by cyclization/dehydration (the cyclization which is accompanied by dehydration; hereinafter referred to as "cyclodehydration") of acetonylacetone ("Die Makromolekulare Chemie", 127, p. 78–93 (1969), and (3) a method which comprises the cyclodehydration of 5-methyl-5-hexen-2-one in the presence of a catalyst such as alumina (U.S. Pat. No. 4,967,033).

From industrial viewpoints, however, the above-mentioned method (1) has a problem that a monomethyl compound or a trimethyl compound is produced as a by-product, and position isomers of dimethyl compounds are also produced as by-products, so that it is difficult to separate singly the 1,3-dimethyl compound. In the above-mentioned method (2), the raw materials are somewhat expensive and particularly the Grignard reagent is very expensive, and what is worse, it is necessary to use quite inflammable ether as a reaction solvent. Moreover, the above-mentioned method (3) is disadvantageous in that, for example, the raw materials are expensive.

SUMMARY OF THE INVENTION

The present invention has been accomplished in view of the above-mentioned circumstances, and an object of the present invention is to synthesize cyclopentadienes at low cost from inexpensive raw materials through a simple reaction.

The first aspect of the present invention is, therefore, directed to a method for producing cyclopentadienes represented by the following structural formula (3) which comprises the step of cyclodehydration of unsaturated carbonyl compounds represented by the following general formula (1) or (2) in a vapor phase in the presence of a solid acid catalyst:

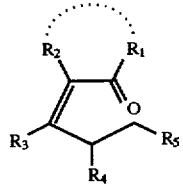

Formula (1)

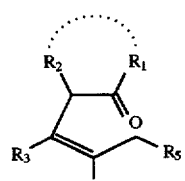

Formula (2)

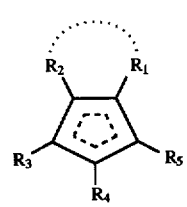

Formula (3)

In the above formulae (1), (2) and (3), $R_1$ to $R_5$ are the same or different groups, and each of $R_1$ to $R_5$ is a hydrogen atom, an alkyl group having 1 to 4 carbon atoms or an aryl group; the dotted line connecting $R_1$ with $R_2$ denotes that an aliphatic five-membered or six-membered ring can be formed; and the dashed lines in the five-membered ring of the formula (3) denote that this five-membered ring contains two carbon-carbon double bonds.

The second aspect of the present invention is directed to the method for producing cyclopentadienes according to the first invention wherein the solid acid catalyst is a synthetic solid acid catalyst, a natural clay-containing solid acid catalyst, a solid acid catalyst obtained by supporting a liquid inorganic acid on a porous inorganic carrier, or a mixture of these catalysts.

The third aspect of the present invention is directed to the method for producing cyclopentadienes according to the second invention wherein the synthetic solid acid catalyst is selected from the group consisting of silica-alumina, silica-magnesia, silica-calcia, alumina, silica, and zeolites.

The fourth aspect of the present invention is directed to the method for producing cyclopentadienes according to the first invention wherein the cyclodehydration is carried out at a temperature in the range of 120° to 600° C.

The fifth aspect of the present invention is directed to the method for producing cyclopentadienes according to the above first invention wherein the cyclodehydration is carried out under a reaction pressure of 10 kg/cm² or lower.

The sixth aspect of the present invention is directed to the method for producing cyclopentadienes according to the first invention wherein the cyclopentadiene is 1,3-, 2,5- or 1,4-dimethyl-1,3-cyclopentadiene, or a mixture of them.

The seventh aspect of the present invention is directed to a method for producing cyclopentadienes which method comprises the following steps of (I) and (II):

(I) the step to select the same or different kinds of ketones or aldehydes or the combination of a ketone and an aldehyde so that the total number of carbon atoms in the reactant molecules is 7 or more, and to react them in the presence of an acid catalyst or a basic catalyst, and (II) the step to subject the resultant reaction product to vapor phase cyclodehydration in the presence of a solid acid catalyst.

The eighth aspect of the present invention is directed to the method for producing cyclopentadienes according to the seventh invention wherein the reaction product of step (I) contains a β-hydroxycarbonyl compound, an α,β-unsaturated carbonyl compound and/or a β,γ-unsaturated carbonyl compound.

The ninth aspect of the present invention is directed to the method for producing cyclopentadienes according to the seventh invention wherein the reaction product of step (I) is subjected to cyclodehydration without purifying it by separating the β-hydroxycarbonyl compound, the α,β-unsaturated carbonyl compound and/or the β,γ-unsaturated carbonyl compound from the reaction product.

The tenth aspect of the present invention is directed to the method for producing cyclopentadienes according to the seventh invention wherein the solid acid catalyst is a synthetic solid acid catalyst, a natural clay-containing solid acid catalyst or a catalyst obtained by supporting an inorganic acid or a heteropolyacid on a porous inorganic carrier.

The eleventh aspect of the present invention is directed to the method for producing cyclopentadienes according to the tenth invention wherein the solid acid catalyst is selected from the group consisting of silica-alumina, silica-magnesia, silica-calcia, alumina, silica, and zeolites.

The twelfth aspect of the present invention is directed to the method for producing cyclopentadienes according to the seventh invention wherein the cyclodehydration is carried out at a temperature in the range of 120° to 600° C.

The thirteenth aspect of the present invention is directed to the method for producing cyclopentadienes according to the seventh invention wherein the cyclodehydration is carried out under a reaction pressure of 10 kg/cm$^2$ or lower.

The fourteenth aspect of the present invention is directed to the method for producing cyclopentadienes according to the seventh invention wherein the cyclopentadiene is 1,3-, 2,5- or 1,4-dimethyl-1,3-cyclopentadiene, or a mixture of them.

The fifteenth aspect of the present invention is directed to the method for producing cyclopentadienes according to the seventh invention wherein at least one of the reactants is a symmetrical ketone.

The sixteenth aspect of the present invention is directed to the method for producing cyclopentadienes according to the seventh invention wherein the combination of the reactants comprises acetone and isobutyraldehyde.

DETAILED DESCRIPTION OF THE INVENTION

The unsaturated carbonyl compounds represented by the general formulae (1) and (2) which are used in the present invention as well as the cyclopentadienes represented by the general formula (3) which are produced by the method of the present invention, are exemplified by the following compounds.

As mentioned above, each of the substituent groups of $R_1$ to $R_5$ in the general formulae (1) to (3) is a hydrogen atom, an alkyl group having 1 to 4 carbon atoms or an aryl groups. The alkyl group is exemplified by methyl, ethyl, n-propyl, isopropyl, n-butyl, isobutyl, and tert-butyl groups. The aryl group is exemplified by phenyl group and naphthyl group which can have lower alkyl substituents such as methyl group and/or ethyl group.

In the first place, when a raw material of formula (1) or (2) in which any one of the substituent groups of $R_1$ to $R_5$ is a methyl group and the other substituents are hydrogen atoms such as 3-hexen-2-one, 4-hexen-2-one, 2-methyl-2-pentenal, 2-methyl-3-pentenal, 4-methyl-2-pentenal or 4-methyl-3-pentenal, is used as an unsaturated carbonyl compound, methylcyclopentadiene is produced as the cyclopentadienes of formula (3).

Furthermore, if a raw material such as 5-methyl-3-hexen-2-one, 5-methyl-4-hexen-2-one, 4-methyl-3-hexen-2-one, 4-methyl-4-hexen-2-one, 2,4-dimethyl-2-pentenal, 2,4-dimethyl-3-pentenal, 3-methyl-2-hexenal or 3-methyl-3-hexenal in which any two of the substituents of $R_1$ to $R_5$ are methyl groups and the other substituents are hydrogen atoms is used as the unsaturated carbonyl compound represented by formula (1) or (2), 1,3-, 2,5- or 1,4-dimethyl-1,3-cyclopentadiene or a mixture of them is produced as the cyclopentadienes of formula (3).

Moreover, if a raw material such as 3-methyl-3-hexen-2-one, 3-methyl-4-hexen-2-one, 3-hepten-2-one, 4-hepten-2-one, 2,3-dimethyl-2-pentenal, 2,3-dimethyl-3-pentenal, 3,4-dimethyl-2-pentenal, 3,4-dimethyl-3-pentenal, 4-methyl-2-hexenal or 4-methyl-3-hexenal is used as the unsaturated carbonyl compound represented by formula (1) or (2), 1,2-, 2,3- or 1,5-dimethyl-1,3-cyclopentadiene or a mixture of them is produced as the cyclopentadienes having formula (3).

If a raw material such as 3,4-dimethyl-3-hexen-2-one, 3,4-dimethyl-4-hexen-2-one, 3,5-dimethyl-3-hexen-2-one, 3,5-dimethyl-4-hexen-2-one, 2,3-dimethyl-2-hexanal or 2,3-dimethyl-3-hexenal in which any three of the substituents of $R_1$ to $R_5$ are methyl groups and the other substituents are hydrogen atoms is used as the unsaturated carbonyl compound of formula (1) or (2), a trimethylcyclopentadiene is produced as the cyclopentadiene of formula (3).

The methyl group having one carbon atom was exemplified above as the alkyl group of the substituents of $R_1$ to $R_5$. However, the unsaturated carbonyl compounds can be similarly exemplified by the compounds in which each methyl group is replaced by an alkyl group having 2 to 4 carbon atoms or an aryl group, e.g., an alkyl group such as ethyl group, propyl group or butyl group, or an aryl group such as phenyl group or naphthyl group. In the above, the aryl group may also be its lower alkyl aryl derivatives such as a methyl-substituted aryl group and ethyl-substituted aryl group.

Furthermore, an unsaturated carbonyl compound having different substituent groups such as two different alkyl groups or aryl groups, can also be used similarly. For example, the compound having a plurality of substituents such as a methyl group and an ethyl group can be used.

The substituent groups $R_1$ and $R_2$ can be bonded to each other to form an aliphatic five-membered or six-membered ring. Typical examples of such compounds include 2-isobutylidenecyclohexanone, 2-(1-isobutenyl)cyclohexanone, 2-isobutylidene-4-methylcyclohexanone, 2-(1-isobutenyl)-4-methylcyclohexanone, 2-isobutylidene-6-methylcyclohexanone, 2-(1-isobutenyl)-6-methylcyclohexanone, 2-(2-ethylbutylidene)cyclohexanone, and 2-(2-ethyl-1-butenyl)cyclohexanone.

Above all, the unsaturated carbonyl compounds in which $R_4$ in formula (1) or (2) is an alkyl group are particularly preferable as raw materials because the cyclopentadienes can be produced in high yields with such compounds even at a low reaction temperature.

Concerning the cyclopentadienes as the products represented by formula (3), 1,3-dialkylcyclopentadienes, particularly 1,3-dimethylcyclopentadiene is preferable, because it has a high thermal stability and it can be obtained in a high yield as an end product.

In the present invention, solid acid catalysts are used. Examples of the preferable solid acid catalysts are synthetic solid acid catalysts such as silica-alumina, silica-magnesia, silica-calcia, alumina, silica, and zeolites, and natural clay minerals such as acid clay and activated clay. Typical examples of the zeolites which are preferably used as the solid acid catalysts include HX-type zeolites, HY-type zeolites, and hydrogen zeolites such as hydrogen mordenite and hydrogen faujasite. Furthermore, an alkali metal such as sodium or potassium can be supported on these solid acid catalysts. The quantity of carbon which is deposited on the catalyst can be reduced by the use of the alkali metal.

In addition, a catalyst obtained by suitably supporting one or more of inorganic acids on a porous inorganic carrier can also be used. Examples of the inorganic acids include phosphoric acid and heteropolyacids such as phosphotungstic acid, silicotungstic acid and silicomolybdic acid. A typical example of such a catalyst is a carrier supported-acid catalyst which is obtained by supporting an inorganic acid on a porous inorganic carriers such as alumina, magnesia, silica or activated carbon.

It is also possible to use a mixture of the above-mentioned various kinds of catalysts.

Concerning the above-mentioned solid acid catalysts, the synthetic solid acid catalysts, particularly silica-alumina, silica-magnesia, silica-calcia, alumina, silica, and zeolites are preferably used in view of the stability of the catalysts. If the high selectivity of reaction is taken into consideration, silica-alumina is more preferable, and especially, HY-type zeolite and hydrogen mordenite are most preferable.

Reaction temperature is selected within the range of 120° to 600° C., preferably 250° to 500° C., in accordance with the catalyst composition, the contact time between a catalyst and raw materials, the molar ratio of diluent to raw materials and so forth. If the reaction temperature is higher than this range, not only the aimed cyclodehydration but also side reactions such as the aromatization of reaction product and the hydrogenation of raw materials and reaction product are rapidly caused to occur, which seriously lowers the selectivity. On the other hand, if the reaction temperature is lower than this range, the rate of the intended cyclodehydration is lowered, which is not desirable in economical viewpoint.

In order to suppress these side reactions owing to the hydrogen which is generated in the reaction system, a hydrogen acceptor such as benzene, tetralin, nitrobenzene, cinnamic acid or benzophenone is added, or alternatively, nitrogen, carbon dioxide or a small amount of oxygen may be fed during the reaction so as to remove the generated hydrogen.

Because the diolefin produced by the reaction is polymerizable, if the diolefin is maintained at a high temperature and a high concentration for a long period of time in a reaction vessel, a part of the produced diolefin is polymerized or dimerized, which leads to the loss of the product. In order to avoid this loss, it is effective to dilute the raw material with an inert gas such as nitrogen, helium, argon or steam. No particular restriction is put on the ratio of dilution.

In the reaction according to the present invention, if the catalyst is used for a long period of time, the activity of catalyst is gradually lowered owing to coking and so forth. Accordingly, the catalyst can be subjected to decoking treatment using, for example, air or the like at a high temperature of about 500° C. so as to recover the initial activity of the catalyst.

The type of reaction may be any of a fixed bed reaction, a moving bed reaction and a fluidized bed reaction. In the reaction, either of a batch process and a continuous feed process can be employed. From an industrial viewpoint, the continuous flow process is preferable.

In the present invention, the catalytic contact must be done while maintaining the raw materials and the reaction product in a vapor phase. A liquid phase reaction, is not desirable because the polymerization or the dimerization of the raw materials or the product is a serious problem.

No particular restriction is put on the reaction pressure so far as the raw materials or the product can be maintained in a vapor phase. The reaction pressure is generally 10 kg/cm$^2$ or lower, and preferably in the range of atmospheric pressure to 5 kg/cm$^2$.

The contact time between the raw materials and the catalyst is in the range of 0.005 to 20 seconds, preferably 0.01 to 10 seconds, and more preferably 0.05 to 5 seconds. If the contact time is shorter than this range, it is not desirable because the rate of reaction is lowered. On the other hand, if the contact time is longer than the above range, side reactions such as the polymerization and the hydrogenation of produced diolefin increase, which undesirably lowers the selectivity of reaction.

The gas discharged from the reaction vessel is immediately cooled to be liquefied. If necessary, the gas may be passed through a liquid absorbing medium such as a hydrocarbon in order to recover the gas.

After the separation of water from oily components, the intended high-purity product can be recovered from the oily components by distillation as occasion demands. The reaction product has generally a boiling point lower than those of the raw materials, and therefore, the product can easily be separated from the raw materials. Among the obtained cyclopentadienes, some compounds are thermally unstable owing to their chemical structures, so that it is sometimes necessary to employ a recovery means which is operated at a low heating temperature such as distillation under reduced pressure.

The present invention comprises the process including steps (I) and (II) which will be hereinafter described.

Step (I):

In step (I) of the present invention, the reaction between ketones, between aldehydes, or between a ketone and an aldehyde is carried out in the presence of an acid catalyst or a basic catalyst.

In the reaction between ketones or between aldehydes, the ketones or the aldehydes can be the same or different ones. One of the ketones or aldehydes to be reacted has at least one active hydrogen atom-on the carbon atom at the α-position relative to the carbonyl group. More preferably, the carbon atom at the α-position of one of the ketones or aldehydes to be reacted has two hydrogen atoms or both of the ketones or aldehydes to be reacted have at least one hydrogen atom at the α-position carbon atom relative to the carbonyl group, respectively.

It is necessary that the number of total carbon atoms of the ketones, the aldehydes or the combination of ketone and aldehyde to be reacted is 7 or more. If the number of the total carbon atoms is less than 7, it is undesirable because the formation of intended cyclopentadiene is difficult. The number of the carbon atoms of the ketone or the aldehyde itself is not limited so far as the number of the carbon atoms in total is 7 or more. For example, a ketone or an aldehyde having 3 to 6 carbon atoms can be used. No particular restriction is put on the upper limit of the number of the total carbon atoms, but it is usually 20 or less.

Typical examples of ketones and aldehydes which can be used in the present invention include acetone and propionaldehyde which have 3 carbon atoms; methyl ethyl ketone, isobutyraldehyde and butyraldehyde which have 4 carbon atoms; diethyl ketone, methyl propyl ketone, methyl isopropyl ketone, valeraldehyde, isovaleraldehyde, 2-methylbutanal and 2,2-dimethylpropanal which have 5 carbon atoms; methyl n-butyl ketone, ethyl isopropyl ketone, ethyl n-propyl ketone, methyl isobutyl ketone, methyl sec-butyl ketone, methyl tert-butyl ketone, cyclohexanone, hexanal, 4-methylpentanal, 3-methylpentanal, 2-methylpentanal, 2-ethylbutanal, 3,3-dimethylbutanal and 2,2-dimethylbutanal which have 6 carbon atoms; 2,3-dimethylpentanal which has 7 carbon atoms; and dibutyl ketone and 2-ethylhexanal which have 8 carbon atoms.

In addition thereto, aromatic carbonyl compounds such as acetophenone and propiophenone, and 2-phenylpropanal can also be used.

In the present invention, it is desirable that a ketone or an aldehyde is used as at least one of the reactant materials, each of which materials has, on the carbon atom of the carbonyl group, at least one branched alkyl substituent group such as an isopropyl group, sec-butyl group or tert-butyl group. When such a ketone or aldehyde is used as the raw material, the yield of intended product, cyclopentadiene, can be raised. Examples of such compounds include isobutyraldehyde and 2-methylbutanal.

For example, when acetone and isobutyraldehyde are used as raw materials, 1,3-dimethylcyclopentadienes are produced; when acetone and 2-methylbutanal are used as raw materials, 1,3-methylethylcyclopentadienes and 1,2,3-trimethylcyclopentadienes are produced; when methyl ethyl ketone and isobutyraldehyde are used as raw materials, 1,3-methylethylcyclopentadienes and 1,2,4-trimethylcyclopentadienes are produced; when diethyl ketone and isobutyraldehyde are used as raw materials, 2,4-dimethyl-1-ethylcyclopentadienes are produced; and when cyclohexanone and isobutyraldehyde are used as raw materials, 2-methyl-4,5,6,7-tetrahydroindenes are produced.

A method of reacting carbonyl compounds such as ketones, aldehydes, or the combination of the ketone and the aldehyde in the presence of the acid catalyst or the basic catalyst, as in step (I) of the present invention, is known as "aldol condensation".

Examples of the catalyst for use in the reaction of step (I) include acids such as hydrochloric acid, sulfonic acid, p-toluenesulfonic acid, zinc chloride and potassium hydrogensulfite; metal hydroxides such as sodium hydroxide, calcium hydroxide, potassium hydroxide and barium hydroxide; a metal alkoxide such as sodium ethoxide; amines such as piperidine, pyrrolidine, 3-methylpyrrolidine and diethylamine; and bases such as alkali carbonates, sodium amide, potassium cyanide and sodium acetate. No particular restriction is put on the amount of the acid catalyst or the basic catalyst to be used, but it is usually employed in an amount of 0.01 to 10% by weight based on the weight of the reactant materials.

As a reaction solvent for use in the reaction of step (I), there can be used suitable solvents which are inert to the reaction, such as water, alcohols, ethers and benzene. Alternatively, the ketone or aldehyde itself which is the reactant material can be used in an excess amount.

No particular restriction is put on the reaction temperature and pressure, so far as the reaction system is maintained in a liquid phase, but in general, the reaction temperature is suitably selected within the range of 0° to 200° C. Furthermore, no particular restriction is put on the reaction time, but in general, it is suitably selected within the range of 1 minute to several tens of hours.

After the completion of the reaction, washing with water and neutralization are carried out to remove the catalyst.

When the reaction is carried out in the presence of a weak basic catalyst, a β-hydroxycarbonyl compound can be obtained mainly. When the reaction is done in the presence of a strong acid catalyst or a strong basic catalyst, a β-hydroxycarbonyl compound is first produced and its dehydration reaction then occurs to produce an α,β-unsaturated carbonyl compound. Furthermore, in the reaction system, this α,β-unsaturated carbonyl compound is sometimes isomerized to produce a β,γ-unsaturated carbonyl compounds. All of these β-hydroxycarbonyl compounds, α,β-unsaturated carbonyl compounds and β,γ-unsaturated carbonyl compounds can be used as raw materials for the subsequent cyclodehydration.

The β-hydroxycarbonyl compound which is obtained by the method of the present invention is represented, for example, by the general formula (4):

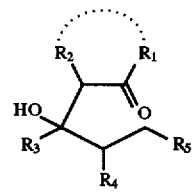

Formula (4)

The α,β-unsaturated carbonyl compound which is obtained by the method of the present invention is represented, for example, by the general formula (1): Formula (1)

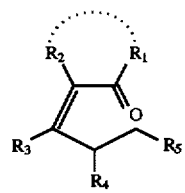

Formula (1)

The β,γ-unsaturated carbonyl compound which is obtained by the method of the present invention is represented, for example, by the general formula (2):

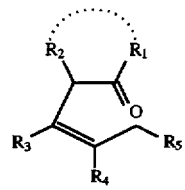

Formula (2)

When these compounds are subjected to cyclodehydration in the next step (II), cyclopentadienes represented by the general formula (3) can be produced:

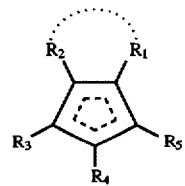

Formula (3)

In the formulae (1) to (4), the substituent groups $R_1$ to $R_5$ are the same or different groups, and each of $R_1$ to $R_5$ is a hydrogen atom, an alkyl group or an aryl group.

Furthermore, each of dotted lines connecting $R_1$ to $R_2$ in the formulae (1) to (4) denote that an aliphatic five-membered or six-membered ring can be formed. The dashed lines in the five-membered ring of the formula (3) denote that the five-membered ring contains two carbon-carbon double bonds. In other words, definitions for the substituent groups of $R_1$ to $R_5$, the dotted line and the dashed line are the same as those in the foregoing ones.

That is to say, in the present invention, after the ketone or the aldehyde was allowed to react, the acid catalyst or the basic catalyst is removed, and the oily portion containing the β-hydroxycarbonyl compound, α,β-unsaturated carbonyl compound, or β,γ-unsaturated carbonyl compound or a mixture of them is then subjected to the cyclodehydration reaction, thereby producing the cyclopentadienes.

Incidentally, it is possible that the β-hydroxycarbonyl compound obtained in step (I) is dehydrated with an acid catalyst or the like in an additional step to convert it into the α,β-unsaturated carbonyl compound, and this compound is further isomerized to the β,γ-unsaturated carbonyl compound. After that, the β,γ-unsaturated carbonyl compound is subjected to the cyclodehydration. Furthermore, it is also possible that the obtained α,β-unsaturated carbonyl compound is isomerized with an acid catalyst or the like in another step to convert it into the β,γ-unsaturated carbonyl compound, and this compound is then subjected to the next cyclodehydration reaction. To the contrary, it is possible that the β,γ-unsaturated carbonyl compound is isomerized into α,β-unsaturated carbonyl compound, which is then fed to the next step (II).

The reaction of step (I) will be described with the examples of ketone and aldehyde which are preferable as the starting materials for the step (I).

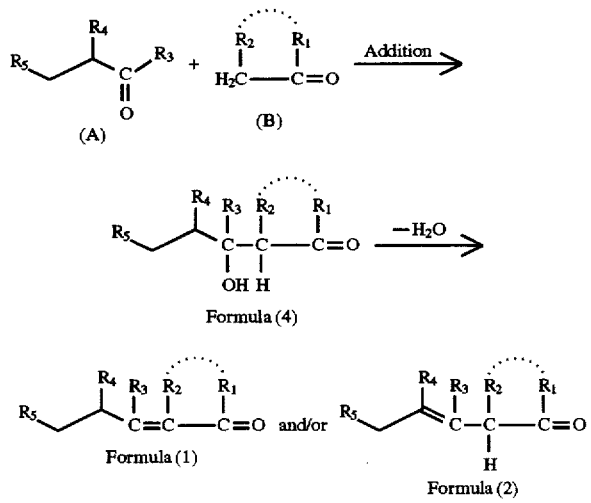

The above carbonyl compounds A and B are ketone or aldehyde, respectively. The compounds A and B can be the same compounds. The definitions for the symbols $R_1$ to $R_5$ and the dotted line connecting $R_1$ with $R_2$ are the same as those in the aforementioned formulae (1) to (4).

As described in the foregoing passage, the ketone or aldehyde A, B are caused to react in the presence of an acid catalyst or a basic catalyst to produce the compounds of formulae (1), (2) or (4) or the mixture of them. It is possible to obtain a reaction product containing mainly any one of the compounds of formulae (1), (2) and (4) or a mixture of them by properly regulating the kind and quantity of the catalyst and conditions of the reaction. Any of the compounds of formulae (1), (2) and (4) can be employed as the starting material for the subsequent step (II).

Accordingly, it is advisable to produce the compound of formulae (1), (2) or (4) or their mixture in accordance with the characteristics of steps (I) and (II). Therefore, if need be, β-hydroxycarbonyl compound of formula (4) is produced in the first step and it is converted into the compound of formula (1) or (2) through the above-mentioned dehydration and, if necessary, through separate isomerization so as to supply it to the next step (II). It is of course possible that the α,β-unsaturated carbonyl compound of formula (1) is produced and it is converted into β,γ-unsaturated carbonyl compound of formula (2) through a separate isomerization process, or vice versa, and the obtained reaction product is then used for the succeeding step (II).

In the above reaction formulae of the aldol reaction, the carbonyl compounds A and B are reacted to produce the β-hydroxycarbonyl compound of formula (4).

When the hydroxyl group of the β-hydroxycarbonyl compound and the hydrogen atom on the α-position carbon atom relative to the carbonyl group, are subjected to dehydration, the α,β-unsaturated carbonyl compound of formula (1) is produced. The above hydrogen atom means the one which is connected to the carbon atom which is bonded to the substituent group $R_2$. Meanwhile, if the hydroxyl group and the hydrogen atom on the γ-position carbon atom is subjected to dehydration, the β,γ-unsaturated carbonyl compound of formula (2) is produced. By the way, the γ-position carbon atom means the one which has a substituent group of $R_4$ and is adjacent to the carbon atom connected to the hydroxyl group. According to the reaction conditions of the aldol reaction, the isomerization of the compound of formula (1) to the compound of formula (2), or the reverse reaction may be caused to occur during the reaction.

If necessary, the obtained β-hydroxycarbonyl compound, α,β-unsaturated carbonyl compound, β,γ-unsaturated carbonyl compound or a mixture of them is refined by separating them with a suitable means such as distillation. Preferably, only the removal of the acid catalyst or the basic catalyst is carried out, and the catalyst-free materials are then fed to the next step (II) without subjecting them to the refining by separation. This procedure is economical because the step of refining by separation can be omitted. It has been confirmed that coexisting unreacted materials and by-products do not produce any undesirable effect in the next step (II) and they do not cause any trouble in the subsequent distillation when the intended cyclopentadienes are recovered.

By the way, the compound 5-methyl-5-hexen-2-one which is used as a raw material in the above-mentioned U.S. Pat. No. 4,967,033 is not produced generally in the above step (I).

Step (II):

In the next step (II), the cyclodehydration reaction is carried out. Examples of solid acid catalysts which are effective for the cyclodehydration reaction include synthetic catalysts such as silica-alumina, silica-magnesia, silica-calcia, alumina, silica, and zeolites, and natural clay-type mineral catalysts such as acid clay and activated clay. Typical examples of the zeolites which can be used as the catalyst include H-type ZSM-5, HX-type zeolite, HY-type zeolite, and hydrogen zeolites such as hydrogen faujasite and hydrogen mordenite. Furthermore, if an alkali metal such as sodium or potassium is supported on these solid acid catalysts, it is possible to reduce the deposition of carbon on the catalyst.

In addition to the above, it is possible to use a catalyst which is prepared by applying one or more acids to a suitable carrier of porous inorganic substances such as alumina, magnesia, silica, and activated carbon. The above acids are exemplified by an inorganic acid such as phosphoric acid and heteropolyacids such as phosphotungstic acid, silicotungstic acid and silicomolybdic acid.

Concerning the above-mentioned solid acid catalysts, the synthetic solid acid catalysts, particularly silica-alumina, silica-magnesia, silica-calcia, alumina, silica, and zeolites are preferably used in view of the stability and other desirable properties of the catalyst. In view of the high selectivity of the reaction, silica-alumina is more preferable and the HY-type zeolites and hydrogen mordenite are particularly preferable.

When the catalyst for the cyclodehydration of step (II) is used for a long period of time, the activity of the catalyst is gradually lowered owing to coking and so forth. Then the catalytic activity can be regenerated by subjecting the catalyst to decoking in the air at a high temperature of, for example, about 500° C.

The temperature for the cyclodehydration reaction in step (II) can be selected within the range of 120° to 600° C., preferably 250° to 500° C. in accordance with the composition of catalyst, the contact time, the molar ratio of dilution medium and so forth. If the reaction temperature is higher than this temperature range, the aromatization of the intended product and a side reaction such as the formation of a cyclomonoolefin probably caused by the hydrogenation of the produced cyclopentadiene with the hydrogen generated by the aromatization reaction are caused to occur in addition to the cyclodehydration reaction. In this case, the selectivity is seriously lowered. On the other hand, if the reaction temperature is lower than this range, the rate of reaction of the intended cyclodehydration is lowered, which is not desirable in view of economy.

The diolefin which is produced by this reaction is a polymerizable diene. If the diolefin is maintained at a high temperature in a concentrated state for a long period of time in a reaction vessel, a part of the produced diolefin polymerizes or dimerizes, which leads to the loss of the product. In order to avoid this loss, it is effective to dilute the material with an inert gas such as nitrogen, helium, argon or steam. No particular restriction is put on the ratio of dilution.

The type of reaction may be any of a fixed bed reaction, a moving bed reaction and a fluidized bed reaction. As far as the raw materials or the product can be to vaporized, no particular restriction is put on the reaction pressure. The pressure is usually 10 kg/cm$^2$ or lower, preferably in the range of atmospheric pressure to 5 kg/cm$^2$.

The contact time between the raw materials and the catalyst is in the range of 0.005 to 20 seconds, preferably 0.01 to 10 seconds, and more preferably 0.05 to 5 seconds. If the contact time is shorter than this range, it is not desirable because the rate of conversion is lowered. On the other hand, if the contact time is longer than this range, side reactions such as the polymerization or hydrogenation of the produced diolefin is caused to occur and the selectivity of the reaction is lowered.

The gas which is discharged from the reaction vessel is promptly cooled to be liquefied. If necessary, the gas may be passed through an absorbing medium such as a hydrocarbon to absorb a liquefied component so as to collect the intended product.

After the separation of water from oily components, the intended high-purity product can be recovered from the oily components by distillation, if necessary. Because the intended product has a lower boiling point than that of raw materials, the product can easily be separated from the raw materials.

According to the present invention, cyclopentadienes which are useful as intermediate compounds for organic synthesis, can be produced in a high yield from inexpensive materials in accordance with a simple reaction process.

The present invention will be described in more detail, however, the scope of the present invention should not be limited to these examples.

In the following examples, it is to be noted that the unit "%" means "% by weight" unless otherwise indicated.

EXAMPLE 1

The particle diameter of a silica-alumina catalyst (trademark: N633L, made by Nikki Chemical Co., Ltd.) was adjusted to 16 to 20 mesh, and 15 ml of the catalyst was then fed into a stainless steel tube having an inner diameter of 12 mm and a length of 1 m. Afterward, 112 g of 5-methyl-3-hexen-2-one and water were continuously passed through the catalyst layer via a preheating tube at flow rates of 15 ml/hr and 60 ml/hr, respectively, and a cyclodehydration reaction was carried out at a reaction temperature of 380° C. (a contact time with the catalyst: 0.34 second).

The reaction mixture obtained from the cyclodehydration was cooled and after a gas and water were removed, the resultant organic layer was analyzed through gas chromatography. As a result, it was understood that the organic layer contained 1.8% of the raw material and 59.1% of the intended product.

In the next step, 85 g of the thus obtained organic layer was distilled under atmospheric pressure to obtain 40.5 g of a fraction of 101° to 104° C. in boiling point. This fraction was compared with separately synthesized pure samples by means of spectrum analysis, and as a result, it was understood that this fraction comprised dimethylcyclopentadienes containing 1,3-dimethyl-1,3-cyclopentadiene as a main component.

EXAMPLES 2 AND 3

The same reactions as in Example 1 were carried out except that reaction temperatures were set to 330° C. and 430° C., respectively, to obtain two reaction mixtures containing respectively 4.5% and 0% of raw materials and 43.0% and 46.6% of the intended product (dimethylcyclopentadienes containing 1,3-dimethyl-1,3-cyclopentadiene as a main component).

EXAMPLES 4 AND 5

The same reactions as in Example 1 were carried out except that HY-type zeolite (made by Shokubai Kasei Kogyo Co., Ltd.) and hydrogen mordenite (made by Toso Co., Ltd.) were used to obtain 90 g and 88 g of reaction mixtures respectively containing 7.1% and 7.7% of raw materials and 50.8% and 53.0% of the intended product (dimethylcyclopentadienes containing 1,3-dimethyl-1,3-cyclopentadiene as a main component).

EXAMPLE 6

The same reaction as in Example 4 was carried out except that water was replaced with 74.7 l/hr of nitrogen as a diluent. The nitrogen gas containing the reaction product was similarly cooled, and it is then introduced into and absorbed by a cumene solution. After a small amount of water was separated from the resultant cumene layer, it was analyzed through gas chromatography. According to calculation excluding the cumene, it was understood that the resultant reaction mixture contained 0.2% of the raw material and 74.0% of the intended product (dimethylcyclopentadienes containing 1,3-dimethyl-1,3-cyclopentadiene as a main component).

EXAMPLE 7

The same reaction as in Example 1 was carried out except that alumina (trademark: N612N, made by made by Nikki Chemical Co., Ltd.) to obtain 75 g of a reaction mixture containing 2.6% of the raw material and 63.9% of the intended product (dimethylcyclopentadienes containing 1,3-dimethyl-1,3-cyclopentadiene as a main component).

EXAMPLES 8 TO 10

The same procedure as in Example 5 was carried out except that reactant materials were replaced with those shown in Table 1, which was followed by distillation under reduced pressure, to obtain fractions also shown in Table 1.

The respective fractions were measured by NMR, infrared spectroscopic analysis and mass spectrometry shown in Table 2, so that it was understood that they comprised the following cyclopentadiene derivatives.

TABLE 1

Raw Materials and Boiling Points of Products

| Example | Raw Material | Boiling Point of Product (°C./torr) |
|---|---|---|
| Ex. 8 | 2-Isobutylidene cyclohexanone | 97–102/50 |
| Ex. 9 | 2,7-Dimethyl-5-octen-4-one | 79–82/50 |
| Ex. 10 | 1-Phenyl-4-methyl-2-penten-1-one | 110–113/3.9 |

TABLE 2

Determination of Structure

| Example | Method | Data |
|---|---|---|
| Ex. 8 | NMR ($^1$H, ppm): | 5.4–5.9(m, 1H), 2.6–2.9(m, 2H), 2.1–2.4(m, 4H), 1.8–2.05(m, 3H), 1.3–1.7(m, 4H) |
| | Infrared spectroscopic analysis (Neat: cm$^{-1}$): | 2950, 2850, 1450, 1380, 1220, 790 |
| | Mass spectrometry: | 134(M, 46), 119(39), 105(100), 91(60), 77(11) |
| | Main structure: | Formula (5) |
| Ex. 9 | NMR ($^1$H, ppm): | 5.7–6.1(m, 2H), 2.7–2.9(m, 2H), 2.1–2.3(m, 2H), 1.8–2.0(m, 3H), 0.8–1.0(d, 6H) |
| | Infrared spectroscopic analysis (Neat: cm$^{-1}$): | 2980, 2950, 1470, 1390, 900 |
| | Mass spectrometry: | 136(M, 17), 93(100), 91(50), 77(52) |
| | Main structure: | Formula (6) |

TABLE 2-continued

Determination of Structure

| Example | Method | Data |
|---|---|---|
| Ex. 10 | NMR ($^1$H, ppm): | 7.1–7.6(m, 5H), 5.9–6.7(m, 2H), 3.0–3.4(m, 2H), 1.5–2.1(m, 3H) |
| | Infrared spectroscopic analysis (Neat: cm$^{-1}$): | 3080, 2985, 2955, 1695, 1605, 1455, 1380, 890, 760, 700 |
| | Mass spectrometry: | 156(M, 100), 155(35), 141(56), 115(51) |
| | Main structure: | Formula (7) |

EXAMPLE 11

The particle diameter of a silica-alumina catalyst (trademark: N633L, made by Nikki Chemical Co., Ltd.) was adjusted to 16 to 20 mesh, and 15 ml of the catalyst was then fed into a stainless steel tube having an inner diameter of 12 mm and a length of 1 m. Afterward, 112 g of 5-methyl-4-hexen-2-one and water were continuously passed through the catalyst layer by way of preheating tubes at flow rates of 15 ml/hr and 60 ml/hr, respectively, and the cyclodehydration was carried out at a reaction temperature of 380° C. (a contact time with the catalyst: 0.34 second).

The thus cyclodehydrated substance was cooled, and after a gas and water were separated, the organic layer was analyzed through gas chromatography. As a result, it was understood that the organic layer contained 0.4% of the raw materials and 63.7% of the intended product.

Next, 84 g of the thus obtained organic layer was distilled under atmospheric pressure to obtain 35.0 g of a fraction of 101° to 104° C. in boiling point.

This fraction was compared with separately synthesized pure samples by means of spectrum analysis, and as a result, it was understood that the fraction comprised dimethylcyclopentadienes containing 1,3-dimethyl-1,3-cyclopentadiene as a main component.

EXAMPLE 12

The same reaction as in Example 11 was carried out except that HY-type zeolite (made by Shokubai Kasei Kogyo Co., Ltd.) was used as a catalyst to obtain 80 g of a reaction mixture containing 0.9% of the raw material and 81.5% of the intended product (dimethylcyclopentadienes containing 1,3-dimethyl-1,3-cyclopentadiene as a main component).

EXAMPLES 13 TO 15

The same procedure as in Example 12 was carried out except that the raw materials were replaced by those shown in Table 3, which was followed by distillation under reduced pressure, to obtain fractions also shown in Table 3.

The respective fractions were measured by NMR, infrared spectroscopic analysis and mass spectrometry shown in Table 4, so that it was understood that they comprised corresponding cyclopentadiene derivatives, respectively.

TABLE 3

Raw Materials and Boiling Points of Products

| Example | Raw Material | Boiling Point of Product (°C./torr) |
|---|---|---|
| 13 | 2-(1-Isobutenyl)cyclohexanone | 97–101/50 |
| 14 | 2,7-Dimethyl-6-octen-4-one | 80–83/50 |
| 15 | 1-Phenyl-4-methyl-2-penten-1-one | 110–113/3.9 |

TABLE 4

Determination of Structure

| Example | Method | Data |
|---|---|---|
| Ex. 13 | NMR ($^1$H, ppm): | 5.4–5.9(m, 1H), 2.6–2.9(m, 2H), 2.1–2.4(m, 4H), 1.8–2.05(m, 3H), 1.3–1.7(m, 4H) |
| | Infrared spectroscopic analysis (Neat: cm$^{-1}$): | 2950, 2850, 1450, 1380, 1220, 790 |
| | Mass spectrometry: | 134(M, 46), 119(39), 105(100), 91(60), 77(11) |
| | Main structure: | Formula (5) |
| Ex. 14 | NMR ($^1$H, ppm): | 5.7–6.1(m, 2H), 2.7–2.9(m, 2H), 2.1–2.3(m, 2H), 1.8–2.0(m, 3H), 0.8–1.0(d, 6H) |
| | Infrared spectroscopic analysis (Neat: cm$^{-1}$): | 2980, 2950, 1470, 1390, 900 |
| | Mass spectrometry: | 136(M, 17), 93(100), 91(50), 77(52) |
| | Main structure: | Formula (6) |
| Ex. 15 | NMR ($^1$H, ppm): | 7.1–7.6(m, 5H), 5.9–6.7(m, 2H), 3.0–3.4(m, 2H), 1.5–2.1(m, 3H) |
| | Infrared spectroscopic analysis (Neat: cm$^{-1}$): | 3080, 2985, 2955, 1695, 1605, 1455, 1380, 890, 760, 700 |
| | Mass spectrometry: | 156(M, 100), 155(35), 141(56), 115(51) |
| | Main structure: | Formula (7) |

EXAMPLE 16

Step (I-1)

In a flask were placed 1392 g (24 moles) of acetone and 500 ml of a 10% aqueous sodium hydroxide solution, and they were then cooled to 10° C. with stirring. Afterward, a mixed solution of 721 g (10 moles) of isobutyraldehyde and 1392 g (24 moles) of acetone was added dropwise at such a rate that the temperature of the resultant reaction mixture did not exceed 15° C., and after the completion of the addition, the reaction was further continued at room temperature for 4 hours. As a result of analysis by gas chromatography, it was understood that isobutyraldehyde had been quantitatively reacted.

The reaction mixture was neutralized with 18% hydrochloric acid and excessive acetone was then distilled off, and at this time, the reaction mixture was separated into two layers, and 1380 ml of an oily layer (an upper layer) was collected. According to analysis by gas chromatography, the oily layer had the following composition:

| Diacetone alcohol | 13.0% |
|---|---|
| 5-Methyl-3-hexen-2-one | 8.8% |
| 5-Methyl-4-hydroxyhexan-2-one | 59.1% |
| Heavy substance | 17.1% |

Step (I-2)

1250 ml of toluene and 1.75 g of p-toluenesulfonic acid were added to 500 ml of the oily layer obtained in the above step (I-1), and the mixture was then heated for 3 hours, while water was removed from the mixture by the azeotropy of toluene and water at the reflux temperature of toluene. According to gas chromatographic analysis, it was confirmed that 5-methyl-4-hydroxyhexan-2-one was completely consumed. After the completion of the reaction, the solution was neutralized with slaked lime, followed by filtration. Furthermore, toluene was removed by distillation under atmospheric pressure to obtain 216 g of a crude product. This crude product was analyzed by gas chromatography, and as a result, it was understood that the crude product had the following composition:

| 4-Methyl-3-penten-2-one | 1.8% |
|---|---|
| 5-Methyl-3-hexen-2-one | 56.8% |
| 5-Methyl-4-hexen-2-one | 5.8% |
| Heavy substance | 33.8% |

Step (I-3)

1250 ml of toluene and 20 g of p-toluenesulfonic acid were added to 500 ml of the oily layer obtained in the above step (I-1) and the mixture was then heated for 10 hours, while water was removed from the mixture by the azeotropy of toluene and water at the reflux temperature of toluene. According to gas chromatographic analysis, it was confirmed that 5-methyl-4-hydroxyhexan-2-one was completely consumed. After the completion of the reaction, it was neutralized with slaked lime, followed by filtration. Furthermore, toluene was removed by distillation under atmospheric pressure to obtain 208 g of a crude product. This crude product was further distilled to obtain 108 g of a fraction having the following composition:

| 5-Methyl-3-hexen-2-one | 75% |
|---|---|
| 5-Methyl-4-hexen-2-one | 25% |

Step (II-1)

The particle diameter of a hydrogen mordenite catalyst (made by Shokubai Kasei Kogyo Co., Ltd.) was adjusted to 16 to 20 mesh, and 15 ml of the catalyst was then filled into a stainless steel tube having an inner diameter of 12 mm and a length of 1 m.

In the next step, 100 ml of a crude reaction mixture obtained in the above step (I-1) and water were passed through the catalyst layer at a reaction temperature of 380° C. by way of preheating tubes at flow rates of 15 ml/hr and 60 ml/hr, respectively, to carry out the cyclodehydration. In this step, the contact time with the catalyst was 0.34 second. The thus obtained reaction mixture was cooled, and after a gas and water were separated, the resultant organic layer was analyzed through gas chromatography. As a result, it was understood that the peak of 5-methyl-4-hydroxyhexen-2-one disappeared and the reaction mixture containing 25.7% of dimethylcyclopentadiene was obtained.

The above-mentioned reaction mixture was distilled under atmospheric pressure to obtain 10.5 g of a fraction of 101° to 104° C. in boiling point. This fraction was measured by nuclear magnetic resonance (NMR), infrared spectroscopic analysis (IR) and mass spectrometry (MS), and as a result, it was understood that the main component of the fraction was 1,3-dimethyl-1,3-cyclopentadiene.

Step (II-2)

100 g of a reaction mixture of step (I-2) was reacted in the presence of a silica-alumina catalyst (trademark: N633L, made by Nikki Chemical Co., Ltd.) in the same manner as in step (II-1), and as a result, peaks of 5-methyl-3-hexen-2-one and 5-methyl-4-hexen-2-one almost disappeared and a reaction mixture containing 42.5% of dimethylcyclopentadienes was obtained.

The thus obtained reaction mixture was distilled under atmospheric pressure in the same manner as in step (II-1) to obtain 25.2 g of a fraction of 101° to 104° C. in boiling point. As a result of NMR, IR and MS analysis, it was understood that the main component of the fraction was 1,3-dimethyl-1,3-cyclopentadiene.

Step (II-3)

50 g of a distillate of step (I-3) was reacted in the presence of a silica-alumina catalyst (trademark: N633L, made by Nikki Chemical Co., Ltd.) in the same manner as in step (II-1), and as a result, peaks of 5-methyl-3-hexen-2-one and 5-methyl-4-hexen-2-one nearly disappeared and a reaction mixture containing 39.3% of dimethylcyclopentadienes was obtained.

The thus obtained reaction mixture was distilled under atmospheric pressure in the same manner as in step (II-1) to obtain 10.8 g of a fraction of 101° to 104° C. in boiling point. As a result of NMR, IR and MS analysis, it was understood that the main component of the fraction was 1,3-dimethyl-1,3-cyclopentadiene.

Step (II-4)

100 ml of distillate of step (I-3) was reacted in the same manner as in step (II-3) except that HY-type zeolite (made by Shokubai Kasei Kogyo Co., Ltd.) was used as a catalyst and reaction temperature was set to 430° C., to obtain 60.8 g of a reaction mixture containing 50.8% of dimethylcyclopentadienes. According to analysis by gas chromatography, the main component of the dimethylcyclopentadienes was 1,3-dimethyl-1,3-cyclopentadiene.

Step (II-5)

Reaction was carried out in the same manner as in step (II-4) except that water was replaced with 74.7 l/hr of nitrogen as a diluent. The resultant reaction mixture was similarly cooled, and then introduced into a cumene solution to absorb the oily component of the crude reaction mixture by cumene. After a small amount of water was separated from the cumene layer, the reaction mixture was analyzed through gas chromatography. According to calculation excluding the cumene, it was understood that the reaction mixture contained 71.8% of 1,3-dimethylcyclopentadiene.

EXAMPLES 17 TO 23

Step (I)

In a flask were placed 2 moles of ketone, ethanol as a solvent and a 10% aqueous sodium hydroxide solution as a catalyst (cf: Table 5). In Example 19, however, 100 ml of a 1N potassium hydroxide-ethanol solution was used as the basic catalyst in place of aqueous sodium hydroxide solution. Next, a mixed solution of 2 moles of aldehyde and 2 moles of ketone was added dropwise thereto at such a rate that the temperature of the resultant reaction mixture did not exceed 25° C., and after the completion of the addition, the reaction was further continued at room temperature for 16 hours.

The reaction mixture was neutralized with 10% sulfuric acid, and the solvent, excess ketone and unreacted aldehyde were then distilled off by an evaporator. For the thus obtained solution, gas chromatographic analysis, infrared spectroscopic analysis and mass spectrometry were carried out, whereby it was confirmed that the main component of the obtained solution was a corresponding hydroxyketone.

Next, 250 ml of hexane and 10 ml of 10% sulfuric acid were added to the solution, and it was then heated for a period of 3 to 6 hours, while water was removed from the reaction system by the azeotropy of hexane and water at the reflux temperature of hexane. According to gas chromatographic analysis, it was confirmed that the corresponding hydroxyketone was completely consumed and a large peak was observed at a shorter position of a GC retention time.

The reaction mixture was neutralized with a 10% aqueous sodium hydroxide solution, and hexane and water were then distilled off under atmospheric pressure, followed by distillation under reduced pressure, to obtain crude products of fractions shown in Table 5. These crude products were analyzed by gas chromatography, infrared spectroscopic analysis, NMR analysis and mass spectrometry, and as a result, it was understood that the main components of the crude products were corresponding enones.

Step (II)

The particle diameter of a hydrogen mordenite catalyst (made by Toso Co., Ltd.) was adjusted to 16 to 20 mesh, and 15 ml of the catalyst was then filled into a stainless steel tube having an inner diameter of 12 mm and a length of 1 m.

Next, 150 ml of a crude reaction product obtained in the above step (I) and water as a diluent were passed through a catalyst layer at a reaction temperature of 330° C. by way of preheating tubes at flow rates of 10 ml/hr and 60 ml/hr, respectively, to carry out a cyclodehydration reaction. The thus obtained cyclodehydrated substance was cooled, and after a gas and water were separated, the resultant organic layer was analyzed through gas chromatography. As a result, it was understood that the peak of the corresponding enone decreased noticeably and a peak having a short GC retention time was observed.

The above-mentioned reaction mixture was distilled under reduced pressure to obtain fractions having boiling points shown in Table 6. These fractions were measured by NMR, infrared spectroscopic analysis and mass spectrometry, and as a result, it was understood that the main components of the fractions were corresponding cyclopentadiene derivatives.

TABLE 5

Raw Materials and Boiling Points of Products in Step (I)

| Example | Aldehyde | Ketone | Ethanol (ml) | Boiling Point of Product (°C./torr) |
|---|---|---|---|---|
| Ex. 17 | Isobutyr-aldehyde | Cyclohexanone | 0 | 91–93/10 |
| Ex. 18 | Isobutyr-aldehyde | Acetophenone | 130 | 107/3 |
| Ex. 19 | Isobutyr-aldehyde | Pinacolone | 100 | 60–64/8 |
| Ex. 20 | Isobutyr-aldehyde | Diethyl ketone | 160 | 72–74/17 |
| Ex. 21 | Isobutyr-aldehyde | Methyl isopropyl ketone | 400 | 65–67/12 |
| Ex. 22 | Isobutyr-aldehyde | Methyl isobutyl ketone | 100 | 78–80/10 |
| Ex. 23 | 2-Ethyl butanal | Acetone | 0 | 76–78/12 |

TABLE 6

Determination of Structure of Product in Step (II)

| Example | Method | Data |
|---|---|---|
| Ex. 17 | Distillation: | 97–101° C./50 torr |
| | NMR ($^1$H, ppm): | 5.4–6.1(m, 1H), 2.4–2.9(m, 2H), 2.1–2.4(m, 4H), 1.7–1.9(m, 3H), 1.1–1.5(m, 4H) |
| | Infrared spectroscopic analysis (liquid film: cm$^{-1}$): | 2950, 2850, 1450, 1380, 1220, 790 |
| | Mass spectrometry: | 134(M, 46), 119(39), 105(100), 91(60), 77(11) |
| | Main structure: | Formula (5) |

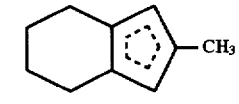

| | | |
|---|---|---|
| Ex. 18 | Distillation: | 122–125° C./7.2 torr |
| | NMR ($^1$H, ppm): | 6.7–7.8(m, 5H), 4.7–6.6(m, 2H), 2.3–3.5(m, 2H), 1.0–1.9(m, 3H), |
| | Infrared spectroscopic analysis (liquid film: cm$^{-1}$): | 3080, 2985, 2955, 1695, 1605, 1455, 1380, 890, 760, 700 |
| | Mass spectrometry: | 156(M, 100), 155(35), 141(56), 115(51) |
| | Main structure: | Formula (7) |

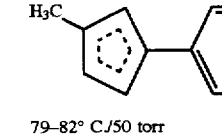

| | | |
|---|---|---|
| Ex. 19 | Distillation: | 79–82° C./50 torr |
| | NMR ($^1$H, ppm): | 4.8–6.3(m, 2H), 2.5–3.0(m, 2H), 1.6–2.3(m, 3H), 1.0–1.4(m, 9H), |
| | Infrared spectroscopic analysis (liquid film: cm$^{-1}$): | 2980, 2950, 1460, 1390, 900 |
| | Mass spectrometry: | 136(M, 23), 121(100), 105(52), 91(21) |
| | Main structure: | Formula (8) |

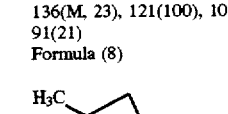

| | | |
|---|---|---|
| Ex. 20 | Distillation: | 67–68° C./50 torr |

TABLE 6-continued

Determination of Structure of Product in Step (II)

| Example | Method | Data |
|---|---|---|
| | NMR ($^1$H, ppm): | 5.0–6.2(m, 1H), 2.6–2.9(m, 2H), 2.3–2.5(m, 2H), 1.7–2.2(m, 6H), 1.0–1.4(m, 3H) |
| | Infrared spectroscopic analysis (liquid film: cm$^{-1}$): | 2980, 2940, 2900, 1455, 1385, 890, 880 |
| | Mass spectrometry: | 122(M, 60), 107(100), 91(70), 79(35) |
| | Main structure: | Formula (9) |

H$_3$C — [cyclopentadiene ring] — CH$_3$ ; H$_5$C$_2$

| | | |
|---|---|---|
| Ex. 21 | Distillation: | 67–72° C./50 torr |
| | NMR ($^1$H, ppm): | 4.9–6.3(m, 2H), 2.4–3.0(m, 2H), 1.7–2.3(m, 4H), 0.9–1.4(m, 6H), |
| | Infrared spectroscopic analysis (liquid film: cm$^{-1}$): | 2980, 2940, 2900, 1460, 1385, 900 |
| | Mass spectrometry: | 122(M, 42), 107(100), 91(63), 79(32) |
| | Main structure: | Formula (10) |

H$_3$C — [cyclopentadiene ring] — C(CH$_3$)$_2$

| | | |
|---|---|---|
| Ex. 22 | Distillation: | 80–81° C./50 torr |
| | NMR ($^1$H, ppm): | 5.7–6.1(m, 2H), 2.4–2.8(m, 2H), 1.7–2.2(m, 5H), 0.8–1.0(m, 7H), |
| | Infrared spectroscopic analysis (liquid film: cm$^{-1}$): | 2980, 2950, 1470, 1390, 900 |
| | Mass spectrometry: | 136(M, 17), 93(100), 91(50), 77(52) |
| | Main structure: | Formula (6) |

H$_3$C — [cyclopentadiene ring] — CH$_2$—CH(CH$_3$)$_2$

| | | |
|---|---|---|
| Ex. 23 | Distillation: | 40–45° C./50 torr |
| | NMR ($^1$H, ppm): | 4.8–6.1(m, 1H), 2.4–2.8(m, 2H), 1.6–2.4(m, 8H), 0.9–1.25(m, 3H), |
| | Infrared spectroscopic analysis (liquid film: cm$^{-1}$): | 2980, 2950, 2900, 1460, 1390, 740 |
| | Mass spectrometry: | 122(M, 45), 107(100), 91(60), 78(38) |
| | Main structure: | Formula (11) |

H$_3$C — [cyclopentadiene ring with CH$_3$] — C$_2$H$_5$

What is claimed is:

1. A method for producing cyclopentadienes which comprises the following steps (I) and (II):

(I) the step of selecting as reactant materials ketones, aldehydes or a combination of a ketone and an aldehyde with the proviso that the total number of carbon atoms in said reactant materials is 7 to 20 and in which at least one of the reactants has at least one active hydrogen on the carbon atom at the alpha-position relative to the carbonyl group, and reacting them in the presence of an acid catalyst or basic catalyst in the liquid phase by an aldol reaction so as to produce a reaction product containing a carbonyl compound selected from the group consisting of a β-hydroxycarbonyl compound, an α,β-unsaturated carbonyl compound, a β,γ-unsaturated carbonyl compound and a mixture thereof, and (II) the step of contacting said carbonyl compound within the temperature range of 120° to 600° C. in a vapor phase and a solid acid catalyst in the presence of an inert diluent, the contact time between said carbonyl compound and the catalyst being within the range of 0.005 to 20 seconds for the cyclodehydration of the carbonyl compound so as to produce the cyclopentadienes.

2. The method for producing cyclopentadienes according to claim 1, wherein the reaction product of said step (I) is cyclodehydrated without separating said β-hydroxycarbonyl compound, α,β-unsaturated carbonyl compound and/or β,γ-unsaturated carbonyl compound from the reaction product.

3. The method for producing cyclopentadienes according to claim 1, wherein said solid acid catalyst is at least one member selected from the group consisting of a synthetic solid acid catalyst, a natural clay-containing solid acid catalyst, a catalyst obtained by supporting an inorganic acid, and a heteropolyacid on a porous inorganic carrier.

4. The methods for producing cyclopentadienes according to claim 3, wherein said solid acid catalyst is a synthetic solid acid catalyst selected from the group consisting of silica-aluminum, silica-magnesia, silica-calcia, alumina, silica, and zeolites.

5. The method for producing cyclopentadienes according to claim 1, wherein said cyclodehydration is carried out under a reaction pressure of 10 kg/cm$^2$ or lower.

6. The method for producing cyclopentadienes according to claim 1, wherein said cyclopentadienes are selected from the group consisting of 1,3-dimethyl-1,3-cyclopentadiene, 2,5-dimethyl-1,3-cyclopentadiene, 1,4-dimethyl-1,3-cyclopentadiene, and a mixture thereof.

7. The method for producing cyclopentadienes according to claim 1, wherein the combination of said reactant materials comprises acetone and isobutyraldehyde.

* * * * *